US012648872B2

(12) United States Patent
Steffensmeier et al.

(10) Patent No.: US 12,648,872 B2
(45) Date of Patent: Jun. 9, 2026

(54) SYSTEMS, APPARATUSES, AND METHODS FOR TREATING BRUXISM, APNEA, AND SLEEP DISORDERS

(71) Applicant: Hawkeye Group, LLC, Roanoke, IN (US)

(72) Inventors: Scott Steffensmeier, Roanoke, IN (US); Jason F. Detweiler, Warsaw, IN (US); Randy Clare, San Juan Capistrano, CA (US)

(73) Assignee: Hawkeye Group, LLC, Roanoke, IN (US)

( * ) Notice: Subject to any disclaimer, the term of this patent is extended or adjusted under 35 U.S.C. 154(b) by 290 days.

(21) Appl. No.: 18/299,256

(22) Filed: Apr. 12, 2023

(65) Prior Publication Data

US 2023/0320893 A1 Oct. 12, 2023

Related U.S. Application Data

(60) Provisional application No. 63/330,045, filed on Apr. 12, 2022.

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ....... A61F 5/56; A61F 5/566; A61F 2005/563
USPC ........................................ 128/848
See application file for complete search history.

(56) References Cited

U.S. PATENT DOCUMENTS

| | | | |
|---|---|---|---|
| 4,801,737 A | 1/1989 | Naito et al. | |
| 8,931,486 B2 | 1/2015 | Halstrom | |
| 9,827,137 B2 | 11/2017 | Schlatter et al. | |
| 9,848,820 B2 | 12/2017 | Chen et al. | |
| 10,687,974 B2 | 6/2020 | Schlatter et al. | |
| 11,007,076 B1 * | 5/2021 | Hamrah ................. | A61B 5/486 |
| 2013/0099918 A1 | 4/2013 | Dunst et al. | |
| 2016/0095740 A1 | 4/2016 | Mardirossian et al. | |

(Continued)

FOREIGN PATENT DOCUMENTS

| | | |
|---|---|---|
| IN | 201611026380 | 7/2017 |
| WO | 2020122394 | 6/2020 |

OTHER PUBLICATIONS

International Search Report and Written Opinion for PCT Application No. PCT/US2023/018294, dated Jul. 24, 2023.

*Primary Examiner* — Adam Baker

(74) *Attorney, Agent, or Firm* — Knobbe, Martens, Olson & Bear, LLP

(57) ABSTRACT

Systems, apparatuses, and methods for aiding a user in ceasing or at least ameliorating sleep or awake bruxism, or apnea, or snoring. The unit is fully enclosed against fluid incursion and placeable between a user's teeth and adjacent cheek, such as while the user is sleeping or awake. A flange extends from a lateral side of the unit, so as to fit between the user's upper and lower teeth and locate the unit in place. The unit includes a circuit that, when completed, such as by the user clenching his/her teeth, causes a mild vibration mechanism to activate and cause a sensation which signals the user to stop clenching his/her teeth. The vibration is preferably such that, if the user is sleeping, the user is not fully awakened but mildly startled to break whatever condition has set off the unit.

4 Claims, 7 Drawing Sheets

(56)     References Cited

U.S. PATENT DOCUMENTS

| | | |
|---|---|---|
| 2017/0290699 A1* | 10/2017 | Radmand ............. A61B 5/4557 |
| 2018/0042760 A1 | 2/2018 | Schlatter et al. |
| 2020/0229966 A1 | 7/2020 | Berk et al. |
| 2020/0345536 A1* | 11/2020 | Letizia ................. A61B 5/4557 |
| 2021/0077013 A1 | 3/2021 | Mistrorigo De Almeida |
| 2021/0145628 A1* | 5/2021 | Ghuge ................. A61B 5/4836 |
| 2021/0330487 A1* | 10/2021 | Kalivoshko ........... A61M 21/00 |

\* cited by examiner

SYSTEMS, APPARATUSES, AND METHODS FOR TREATING BRUXISM, APNEA, AND SLEEP DISORDERS

CROSS-REFERENCE TO RELATED APPLICATIONS

This application claims the benefit of U.S. Provisional Application No. 63/330,045 filed Apr. 12, 2022, the contents of which are incorporated herein by reference.

BACKGROUND OF THE INVENTION

The present invention relates to a systems, apparatuses, and methods useful for treatment of bruxism, apnea and sleep disorders and related symptoms such as facial pain, tension headache, snoring and daytime sleepiness.

It has been determined that a number of medical disorders appear to be related to partial or sometimes complete collapse and obstruction of a person's pharyngeal airway during sleep. Snoring and sleep apnea are two such disorders, typically caused by narrowing of an individual's airway because of the relaxation of the muscles and ligaments in the oropharynx during all stages of sleep but particularly during REM. The jaw drops open which allows translation of the mandible pressing the base of the tongue and soft palate against the pharyngeal wall. Obstructive sleep apnea is a potentially lethal disorder in which breathing ceases during sleep due to complete airway collapse. Snoring is the sound of a partially obstructed airway; air flow comes through a narrow space creating turbulence resulting in vibration of the oral tissues as a sleeping person breathes.

Some prior art approaches to at least snoring as a sleep disorder have been proposed using some kind of device or appliance that position and support the jaw during sleep. It has been recognized that positioning the mandible (lower jaw) forward relative to the maxilla (upper jaw) can eliminate or reduce snoring by supporting the tissues of the oropharynx causing the air passage to remain open. For one example, a user would wear such a device at night to fix the mandible in an anterior, protruded (i.e., forward) position. Such dental appliances essentially consist of acrylic or elastomeric bite blocks, similar to orthodontic retainers or athletic mouth guards, which are custom-fitted to the user's upper and lower teeth, and which may be adjusted to vary the degree of anterior protrusion or simply increasing the occlusal space to allow room for the tongue to posture forward during sleep. See, e.g., U.S. Pat. No. 4,901,737.

While some of these prior art dental appliances have proven effective in maintaining the mandible in a protruded position to improve and maintain air passage, they can have undesirable side effects (https://jcsm.aasm.org/doi/10.5664/jcsm.4858). One of the most common side effects is aggravation of the temporomandibular joint and related jaw muscles and ligaments, especially in individuals who have a tendency to grind their teeth during sleep. This is known as bruxism, a parasomnia which has been defined by the American Academy of Sleep Medicine as the repetitive jaw muscle activity characterized by the clenching or grinding of teeth and/or bracing or thrusting of the mandible (*International Classification of Sleep Disorders*. 3rd ed. Westchester, Darien, Illinois: American Academy of Sleep Medicine; 2014. American Academy of Sleep Medicine. Sleep related bruxism). Bruxism is most often defined by when it occurs. "Awake" bruxism is mainly the clenching of the teeth; "sleep" bruxism is typically much more aggressive and affects the muscles and ligaments of the airway as well as the dentition. Accordingly, many individuals suffering from sleep apnea and snoring disorders are not able, or unwilling, to tolerate existing anti-snoring dental appliances for long periods of time because the appliances break down or the patient finds the appliance too restrictive.

Sleep Bruxism commonly co-occurs with OSA, and the prevalence has been measured in some studies as greater than 50%. (Martynowicz H, Gac P, Brzecka A, Poreba R, Wojakowska A, Mazur G, Smardz J, Wieckiewicz M. The Relationship between Sleep Bruxism and Obstructive Sleep Apnea Based on Polysomnographic Findings. J Clin Med. 2019 Oct. 11; 8(10):1653. doi: 10.3390/jcm8101653. PMID: 31614526; PMCID: PMC6832407). Bruxism has its own deleterious physical and biological consequences. Physical implications include tooth wear, cavities, tooth fracture, restoration fracture and implant failure Biologic implications include hypersensitivity, hypermobility, hypercementosis, periodontal damage, pulpitis, pulpal necrosis, ridge resorption, torus mandibularis, tongue cheek indentation and scalloping, lip cheek or tongue biting, masticatory muscle pain, tmj pain, tmj disc displacement, tmd headache and jaw function disabilities. People may wear mouth guards to prevent enamel wear, face pain or headache, but these devices often do not prevent or mitigate the underlying parasomnia, if present. (Yap A U, Chua A P. Sleep bruxism: Current knowledge and contemporary management. J Conserv Dent. 2016 September-October; 19(5):383-9, doi: 10.4103/0972-0707.190007. PMID: 27656052, PMCID: PMC5026093.)

Biofeedback is a process which uses instruments to provide information about an activity which allows a user to change his/her behavior relative to that activity. Bruxism being a reflexive chewing activity, such as teeth clenching, grinding, bracing and thrusting of the mandible, when conscious attention is distracted, such as during sleeping, subconscious processes can run unchecked, allowing bruxism to occur. Apnea and snoring are likewise unconscious activities which may be positively influenced by use of biofeedback.

BRIEF SUMMARY OF THE INVENTION

The intent of this section of the specification is to briefly indicate the nature and substance of the invention, as opposed to an exhaustive statement of all subject matter and aspects of the invention. Therefore, while this section identifies subject matter recited in the claims, additional subject matter and aspects relating to the invention are set forth in other sections of the specification, particularly the detailed description, as well as any drawings.

The present invention provides, but is not limited to, systems, apparatuses, and methods capable of use to treat bruxism, apnea, sleep disorders, and related symptoms.

The present disclosure relates to development of a centralized "chassis system" as the foundation for treatment of one or most preferably all of apnea, snoring and bruxism. Further advantages can include treatment for related symptoms such as facial pain, tension headache, and daytime sleepiness. The chassis is the outer form of the unit, or shell, having an interior including operational material of the device. The unit is enclosed or encapsulated, and liquid proof against fluid incursion to the interior, as it is intended to be emplaced in a person's mouth. In a preferred form, alterations of the electronics/sensors inside each unit allow for easy modifications and can accommodate technological improvements, while benefiting from the unique and comfortable design. While the chassis system may be considered one of the better embodiments, it will be understood that aspects of the invention can be presented in singular or various mixed embodiments. Embodiments may include the following features:

Diagnostic Device—this would be a product to answer the question, "Do I brux?". It helps to determine or guide a person if clenching their teeth. A user would wear this device and sensors could measure and record information. Perhaps meaningful information is focused around the # of clenches, magnitude of clenches (force), intensity, frequency, etc. The intent is for this form of the disclosure to then guide the user to a solution, most preferably within this same chassis adapted for other issues beyond solely bruxism.

Chassis Puck—this would be the preferred core device, inclusive of electronic circuitry, that provides biofeedback through vibration, such as to reduce jaw tensioning. The fundamental principle of biofeedback causes the subject to minimize the number and magnitude of clenches subconsciously, thus resolving the subsequent issues attributed to bruxism (headaches, tooth damage, TMJ issues, stress, etc.).

Smart Puck—this would be the core device (of #2 above) with the addition of bluetooth communication to facilitate an output to an apparatus, smartphone or the like, which would be able to count, trend, and confirm frequency and duration of a consumer's jaw tensioning habits.

Rechargeable Puck—this would be the core Chassis Puck device or Smart Puck device (of #2, #3 above) with the substitution of rechargeable batteries and external facing contacts or other electrical interface, to allow for, e.g., nightly charging. This would likely be most useful when paired with bluetooth functionality or heavy (extended) users, due to the larger battery drain in those cases.

Sleep Apnea/CPAP Solution—in this aspect of the disclosure, there would be utilization of one or more of the foregoing Pucks combined with other sensors to monitor vital outputs like respiration, heart rate, blood oxygen, as with an associated blood oximeter. Blood oxygen levels go down in apnea conditions. If a threshold is reached, in this aspect of the disclosure, the unit provides biofeedback based on the conditional outputs to address sleep apnea. As a further possibility, one or more body position sensors may provide biofeedback when the wearer lays on their back. This is of interest for the 70% of patients who suffer from positional snoring. Actigraphy will measure body movements to establish sleep stage.

Anti-Snoring Device—in this form, utilization of the Puck would monitor outputs related to snoring and then provide biofeedback based upon the conditional outputs to assist with the reduction of snoring. The devices, when combined with bluetooth capability, could also pair with additional external devices to aid in the reduction of snoring, such as bed or pillow inflation, bed position adjustment via electric motor, alarms, etc.

Advanced Health Tracking Device—in a further form, the Puck may contain an array of health sensors including hydration sensor, Pulse Oximeter and IoT software interface with any smart device. Software calculations include hydration index, SPO2, pulse rate, pulse rate variability, respiration rate, Pleth variability index, perfusion index, pedometer, body position and actigraphy.

In a preferred form, the present disclosure relates to devices that aid a user in ceasing or at least ameliorating bruxism, or apnea, or snoring, by using a unit that is held in the mouth, as between a cheek and jaw. The unit is fully enclosed against fluid incursion, with all of its electronics contained within the so-called chassis. The unit, referred to generally as a "Puck" herein, due to its overall design look in one form, may be placed between a user's teeth and adjacent cheek (oral vestibule), such as while the user is sleeping or awake. A flange or the like extends from a lateral side of the unit, so as to fit between upper and lower teeth and locate the unit in place. In general, the devices include a circuit that, when completed, such as by the user clenching his/her teeth, causes a mild vibration mechanism to activate and cause a sensation which signals the user to stop clenching his/her teeth. It is most preferred that this mild vibration is such that, if the user is sleeping, it does not fully awaken the user, but is of a sufficient quality as to mildly startle the user and break whatever condition has set off the unit. The vibration may also commence with a light vibration and gradually increase the strength and/or length of the vibration if clenching does not cease. Preferably, these are adjustments that can be made by the user.

The invention offers a unique set of advantages to treating bruxism, apnea and snoring. As used herein, "treating" means attempting to address one or more of these issues in a manner to at least reduce if not completely eliminate the condition, as in therapy for the same. In addition to providing a protective barrier between upper and lower teeth, the device employs a benign and inconspicuous biofeedback response to clenching. This biofeedback signal can also be triggered by an associated device for detecting sleep apnea. One such would be a pulse oximeter worn by the user, which measures both pulse rate and blood oxygen concentration. In the case of an apnea event, the oxygen level falls, as the person has ceased or at least interrupted breathing. If the blood oxygen dips below a threshold, a signal is generated which is received wirelessly by the unit. The vibratory mechanism then awakens the patient slightly changing their sleep stage, resolving the OSA event.

Similarly for snoring, an acoustic device is associated with the unit in one form of the invention. That acoustic detects sound indicative of snoring, and then gently provides the biofeedback vibration that will alert the user restoring tissue tone in the throat/Oropharynx, to restore airway patency and eliminate the snoring.

The nature of the preferred biofeedback signal does not use electrical shocks or noises that would irritate the user or others around them. Also, the preferred low profile design does not block the user's airway or limit their ability to talk. Also, the unit is worn inside the mouth so it cannot be seen by others. This allows the user to obtain the relief they need without the embarrassment or stigma that other devices cause.

In an aspect, a unit or appliance for detecting and treating teeth clenching, or apnea or snoring is disclosed. The device may include a first housing containing a power source, such as a battery, a vibration device connected to the power source, and an electrical contact mechanism having a movable element which closes a circuit to actuate the vibration device. A disk-shaped portion may be disposed around the first housing and is adapted to be emplaced in a person's oral vestibule between a cheek and adjacent teeth. A resilient bite portion extends from the first housing and is adapted to be emplaced between upper and lower teeth. The bite portion may have an interior area which is compressible, such as by upper and lower teeth moving toward each other. A compressible element may be disposed in the interior area. The compressible element may cause the movable element of the electrical contact to close to actuate the vibration device in response to compression of the bite portion.

The compressible element may be an elongated stiff part that extends within the bite portion and has an end with a part that engages the movable element as a lever end. The elongated stiff part causes the lever end to apply a force to the movable element to thereby close the circuit in response to compression, for example caused by a user clenching his/her teeth.

The compressible element may be a substantially u-shaped piece having opposed elongated stiff arms and a base, wherein the base is bendable outwardly when the arms are moved toward one another. In this aspect, the base presses the movable element to thereby close the circuit in response to being bent outwardly. The compressible element may be an encapsulated medium that is adapted to bulge toward the movable element to close the circuit in response to compression, for example caused by a user clenching his/her teeth. The medium may be a gas, a liquid, a soft solid, small beads, or any combination thereof.

In an aspect, a dental appliance for detecting and treating teeth clenching may include a first housing adapted to fit between a person's oral vestibule and adjacent upper and lower rows of teeth, wherein the housing has an interior chamber. A power source, a signal generator powered by the power source, and a signal generator powered by the power source are disposed within the chamber. A resilient bite portion extends from the first housing and is adapted to be emplaced between upper and lower teeth. The bite portion also has an interior area which is compressible, as by upper and lower teeth moving toward each other, to actuate the signal generator to generate a signal. A responsive device is in communication with the signal generator which responds to the signal.

The bite portion may not necessarily be compressible in forms of the invention intended not to treat bruxism, as for apnea and snoring. For the latter conditions, the unit would include circuitry to receive a signal from some associated detection device, which signal then triggers the desired biofeedback vibratory response.

In another modification of the disclosure, the device may include an electrical signal generating mechanism of its own. This could be useful for the treatment of bruxism, for instance, where the unit's signal provides a sensory indication to the person, for example, the sensory indication may be an audible sound, a physical sensation, such as a vibration, and any combination of audible and physical sensations. In an aspect, the responsive device is a vibrator that engages some part of the person's body, and is actuated in response to a signal indicative of a teeth clenching threshold force value.

In its most preferred form, the unit has a common chassis which is capable of adaptation for any or all of the conditions sought to be treated. If for more than one condition, a simple switching mechanism may be employed to activate the unit for one or more of bruxism, apnea or snoring. Alternatively, appropriate modules may be provided which are readily installed within the puck for the chosen condition, along with any associated external devices in a kit.

It will be understood that related symptoms such as facial pain, tension headache, and daytime sleepiness may be advantageously addressed in forms and aspects of the invention.

The advantages and aspects of the invention may be further understood upon consideration of the following detailed description, taken in conjunction with the drawings.

BRIEF DESCRIPTION OF THE DRAWINGS

Embodiments of devices, systems, and methods are illustrated in the figures of the accompanying drawings which are meant to be exemplary and not limiting, in which like references are intended to refer to like or corresponding parts, and in which.

DETAILED DESCRIPTION OF THE INVENTION

Detailed embodiments of devices, systems, and methods are disclosed herein. However, it is to be understood that the disclosed embodiments are merely exemplary of the devices, systems, and methods, which may be embodied in various forms. Therefore, specific functional details disclosed herein are not to be interpreted as limiting, but merely as a basis for the claims and as a representative basis for teaching one skilled in the art to variously employ the present disclosure.

Figure 1:
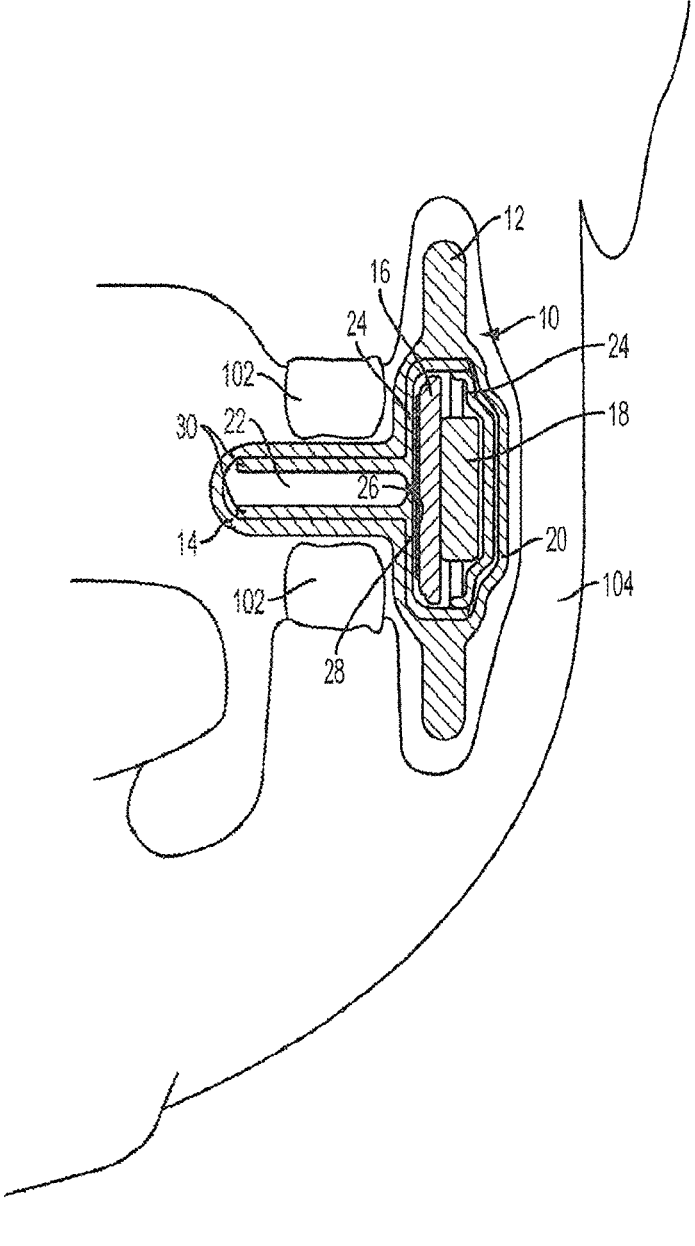
FIG. 1 illustrates a sectional side view of a device in one form of the present disclosure as shown in a user's mouth.
Figure 2A:
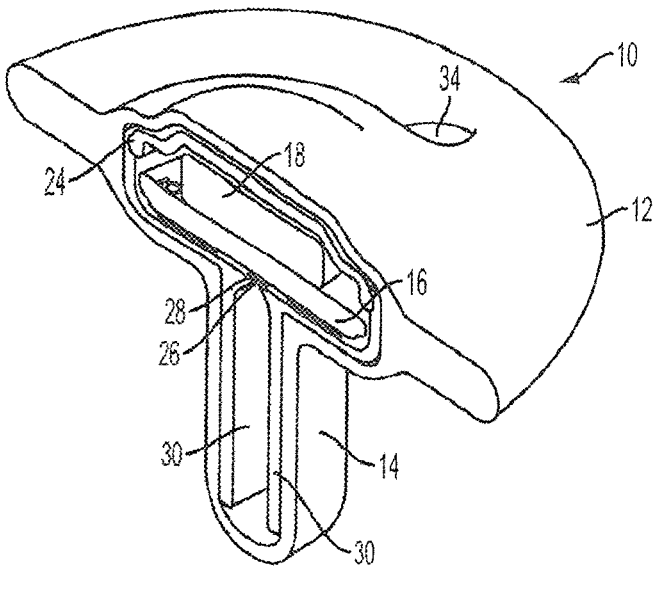
FIG. 2A illustrates a perspective sectional view of the device of FIG. 1.
Figure 2B:
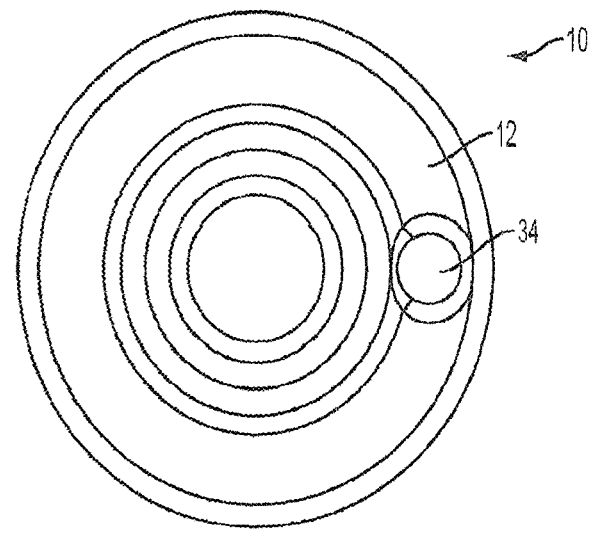
FIG. 2B illustrates a top view of the device of FIG. 2A.
Figure 2C:
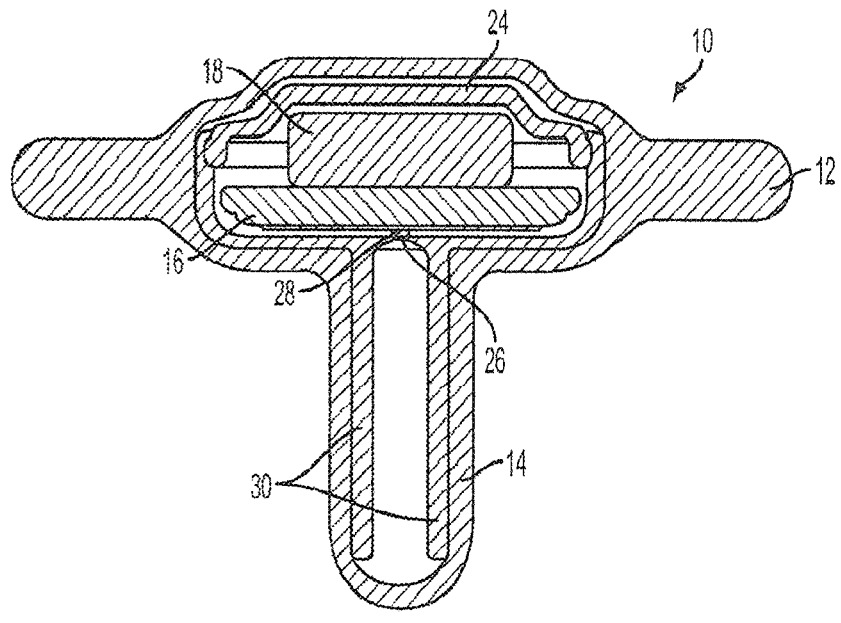
FIG. 2C illustrates a sectional side view of the device of FIG. 2A.
Figure 2D:
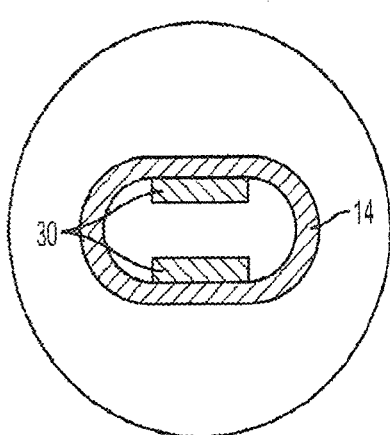
FIG. 2D illustrates a sectional bottom view of the device of FIG. 2A.
Figure 3:
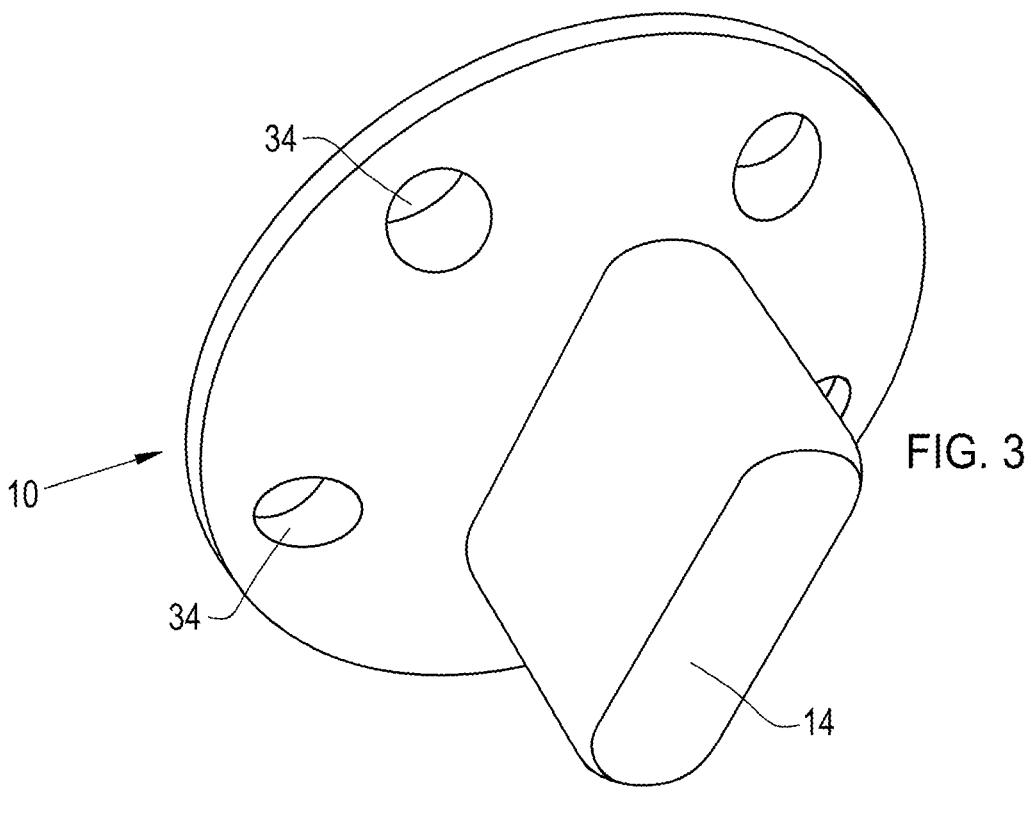
FIG. 3 illustrates an external perspective view of a finished embodiment of the type illustrated in FIGS. 1 through 2A-D, with the bite engaging portion prominent.
Figure 4:
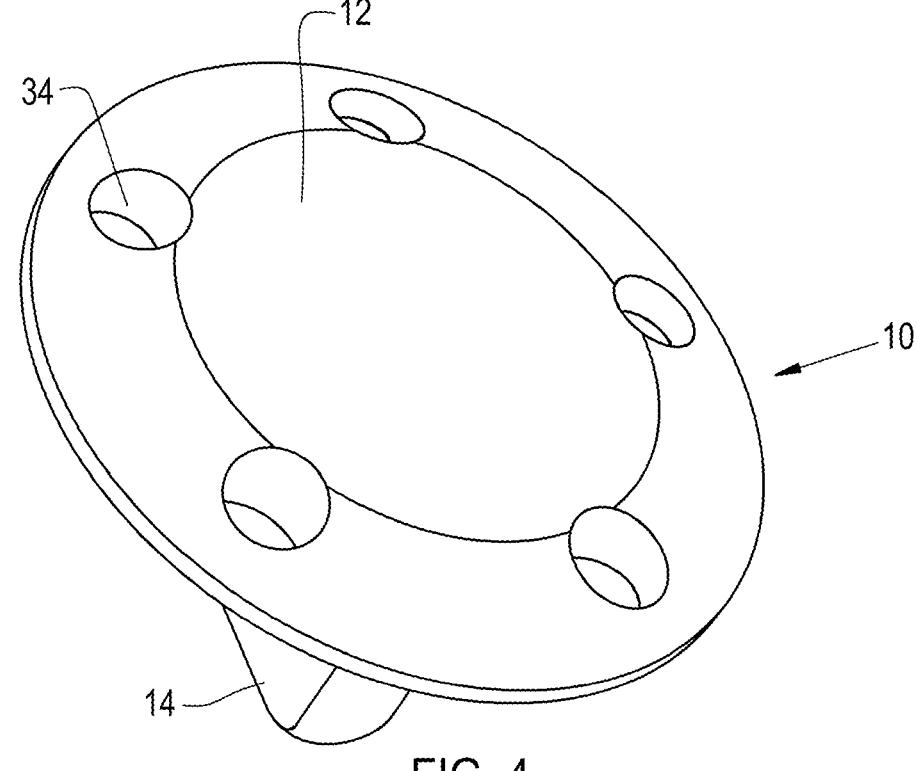
FIG. 4 is a perspective view of the device of FIG. 3, taken from the cheek engaging side.

FIGS. 1-3A-B illustrate a device 10 adapted to provide a signal/sensory indication to a user in response to, in one aspect, the user clenching his/her jaw, or clenching or grinding his/her teeth 102, for example during bruxism. According to other aspects, such a device functions as a "chassis" for use in treating apnea, snoring, and potentially other issues. The device 10 may be used as a training device that provides a reminder to the user in the form of a vibration sensation, an audible sound, an olfactory sensation, a visual indication, a taste sensation, or other sensory indication in response to the physical activity of teeth clenching or bruxism. As illustrated in FIG. 1, the device 10 includes a disc-shaped portion 12 shaped and formed to nest between a cheek 104 and adjacent teeth 102; hence the reference to the so-called "Puck." The device 10 also includes a bite portion or tab 14 that extends and is adapted to situate between the user's teeth 102. When the user clenches his/her teeth 102 the user places pressure on the tab 14. The tab 14 serves to otherwise position and locate the device 10 in its desired place.

The disc-shaped portion 12 and the tab 14 or bite portion are shaped to both maintain patient comfort while anchoring the device 10 in the user's mouth at an optimal position for proper function. For example, the disc-shaped portion 12 is shaped to comfortably fit between the user's cheek 104 and teeth 102, and allows the device 10 to maintain position in the user's cheek pocket. Similarly, the length of the tab 14 is designed to prevent the device 10 from being pushed out from between the user's teeth 102 into the user's cheek pocket, and to limit interference with the user's tongue.

The tab 14 is compressible and includes a mechanism that when compressed activates electronic components in the disc portion of the device 10. When activated, the electronic components (for example, including a power source, such as battery 16, and a responsive device, such as vibrator 18, deliver a vibrating sensation to the user. This vibration sensation provides a signal, such as a biofeedback signal, to the user. That feedback can be in the instance of teeth clenching, or detected apnea (interruption of breathing), or snoring. As will be further described hereafter, there are anticipated associated apparati which will serve to detect conditions beyond bruxism that the device, system and method are intended to ameliorate. So, in the case of bruxism, the device allows the user to take corrective action. The cessation of clenching quickly becomes a natural and automatic response to the vibration reminder. In this way, the device 10 provides a biofeedback response useful in training the user to correct teeth clenching/bruxism.

The device 10 may be formed having a continuous outer wall 20. In this embodiment, such outer wall 20 is formed from a deformable material, preferably medical grade plastic common to dental applications, such that when a user clenches his/her teeth 102 the tab 14 deforms. Outer wall 20 defines an inner chamber 22 which is formed within both the disc-shaped portion 12 and the tab 14. A housing 24 is carried in inner chamber 22, such housing encapsulating the vibrator 18 and the battery 16. The housing 24 completely surrounds the battery 16 and the vibrator 18 such that if outer wall 20 is pierced or otherwise ruptures, the battery and the vibrator will remain encapsulated and protected against fluid incursion. The housing 24 is preferably formed in two parts which snap together to allow assembly of the battery 16 and vibrator 18 and associated electrical conductors prior to enclosing the housing in the outer wall 20.

A diaphragm or thinned section 26 is formed in housing 24 on the face of the housing which is oriented in the direction of tab 1 (i.e., inboard). The thinned section 26 is shaped such that it repeatedly bends or deforms in the same direction, namely in the direction of battery 16. The thinned section 26 is bendable or deformable and facilitates activation of the vibrator 18 as described below. In this embodiment, the thinned section 26 is a single crease in housing 24. A contact element, for example, electrical conductors 28 or a signal generator, which are in electrical communication with vibrator 18, are mounted to housing 24 proximate the inner side of thinned section 26. Battery 16 is positioned adjacent electrical conductor 28, such that when a user is not clenching his/her teeth, the electrical conductor is spaced from battery 16 in an open circuit position. When a user does clench his/her teeth, thinned section 26 bends, thereby pushing or moving the electrical conductor 28 against battery 16 which completes a circuit, allows a signal to flow to vibrator 18, and causes vibrator 18 to activate. As such, when tab 14 is not deformed, a gap is present between electrical conductor 28 and battery 16, which gap is bridged by movement of thinned section 26 which is facilitated by deformation of tab 14.

As will be discussed below, in its form for treating apnea or snoring, a receiver will take the place of the signal generator, or be in addition to the signal generator. That receiver wirelessly interconnects with an external appliance/apparatus, which can send a signal to the receiver to then actuate the vibrator 18.

Turning back to the chassis, sometimes referred to herein as a puck (due to its general overall external look in this particular form), Chassis/device/puck 10 uses a tab 14 that has a generally elongate cross-section, such as an oval-shaped cross-section. This elongate shape helps to orient biofeedback device 10 between the teeth, wherein the device 10 will tend to naturally rotate such that the longer axis of the tab 14 will orient generally parallel with the user's teeth.

Disc-shaped portion 12 is formed having an aperture 34 (FIG. 2A, 2B) passing therethrough, such that aperture 34 forms a hole through the outer flange portion of biofeedback device 10. Aperture 34 does not provide access to internal chamber 22, since this would allow saliva and other fluids to potentially spoil the internal electronics. Instead, aperture 34 allows air to pass through biofeedback device 10 in the case where biofeedback device 10 becomes lodged in the user's airway. In this way, aperture 34 is a safety feature which prevents suffocation.

In one embodiment, a pair of elongate arms 30 extend from housing 24, wherein the arms are spaced on either side of thinned section 26. Arms 30 extend within internal chamber 22 in tab 14. Arms 30 are positioned parallel one another. Arms 30 are wider than they are thick, such that a space is formed between the arms when tab 14 is not clenched. When tab 14 is clenched, arms 30 are forced toward each other which causes thinned section 26 to deform and to push electrical conductor 28 against battery 16. The arms 30 are preferably oriented parallel with the longer axis of tab 14, such that a user's bite motion will cause the arms 30 to move toward each other, rather than biting on the edges of the arms.

As described above, the device 10 uses a lever-type mechanism, which has one or more elongated elements, arms 30, in the bite area that, when moved toward the longitudinal axis of the bite area, cause a movement of the contact element, electrical conductor 28, so as to close a circuit and thereby generate a signal. Such a signal can be an electrical current, to actuate the vibrator 18, for example. In one such embodiment described, there are two elongated arms 30 connected through a base, thinned section 26, of what constitutes a u-shaped piece. As the arms 30 bend toward one another under influence of teeth moving toward engagement (clenching), the base flexes. The base flexes outwardly (essentially bulging), to thereby move the contact element to close a circuit. The base could just as easily move inwardly, and thereby lever the contact to a closed position.

The embodiments described above are very similar in concept in treating bruxism, that a bulging movement physically engages the contact element to close a circuit. One of elongate members 32 or elongate arms 30 defines an actuating member. Actuating member is such that, when a user bites tab 14, the actuating member is actuated in a way that completes a circuit and activates vibrator 18. Housing 24 is optional; the electrical components may be placed directly within inner chamber 22 and actuated directly by the actuating member.

The devices 10 described above involves a single integrated unit which is emplaced in a person's cheek. All of the electronics, power source and indicator device for providing an impulse to the user of teeth clenching (e.g., a vibrator), are contained in that integrated unit.

Figure 8:
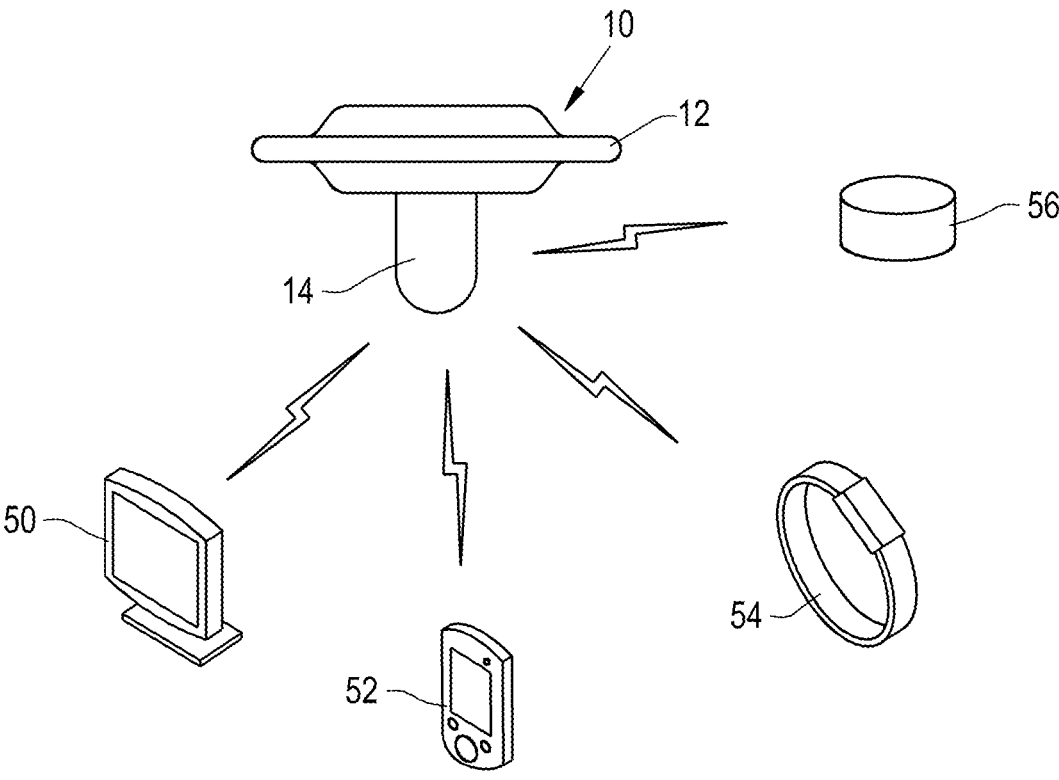
FIG. 8 is a schematic of communications from a device of the present invention with associated external devices.

The embodiments are not limited to an integrated device 10 with all operational elements located in a person's cheek. As illustrated in FIG. 8, the clenching action, or some other action, may result in a signal transmitted, such a through Bluetooth, infrared or radio frequency communication, from the action of the bite area to a remote station or device, such as a computer 50, a mobile phone or handheld device 52, or a smart watch 54, or a web engaged apparatus such as a voice controlled interactive personal assistant 56 (e.g., an Alexa apparatus), among other things. The signals can be generated by the device 10 for recording, use or analysis by such external apparati, as well as for sending signals to the device 10, which then provides some stimulus to the person. Besides vibratory responses, the stimulus could be a visual stimulus, audible sound or alarm, for example, or it could be another physical stimulus, such as a vibration through some mechanism engaging or attached to a person (e.g., the smart watch 54), but which is remote from the general housing of the device 10. Additionally, the device 10 may include circuitry adapted to receive and transmit data and other information to the remote station or external apparatus.

Figure 5:
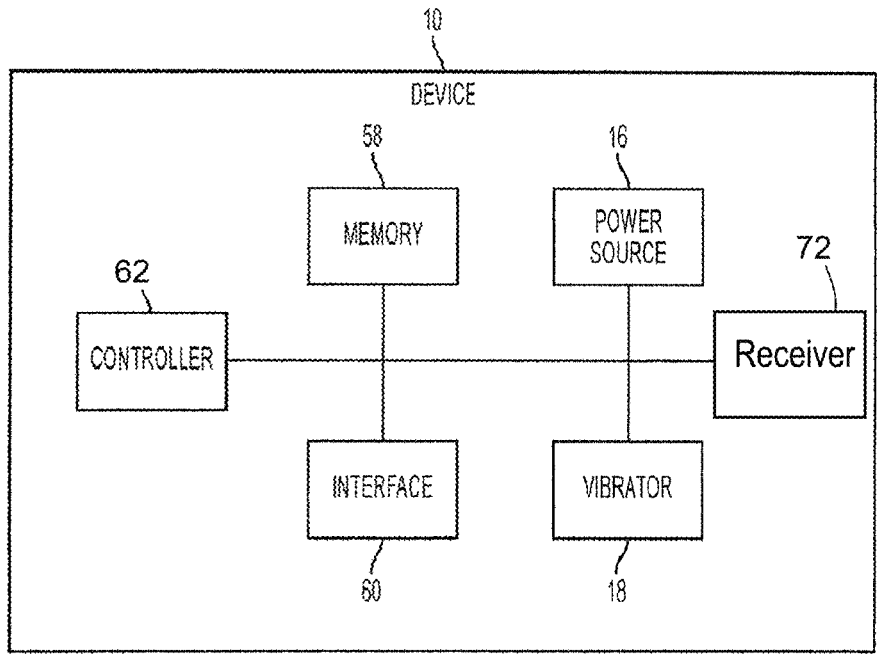
FIG. 5 illustrates a block diagram of circuitry of one form of a device of the present disclosure.

A functional block diagram of components of the device 10 in one form are described with reference to FIG. 5. As illustrated in FIG. 5, the device 10 may include a controller 62 and a memory 58 coupled to the controller 56. The device 10 also includes interface circuitry 60 which may include, for example, a universal serial bus (USB) port, Firewire port, infrared data transmitter, radio frequency data transmitter, Bluetooth, or other communication technique. The interface 60 allows the device 10 to communicate with other external appliances such as, those illustrated in FIG. 8. The interface 60 may also be used to power or charge the power source or battery 16 of the device 10 in a wireless fashion.

The interface 60 and memory 58 may be coupled to the controller 62 by one or more internal signal paths. The controller 56 may be a processor, a control circuit, etc., and may facilitate communication between various components of the device 10 and control operation of various electrical components of the device 10. In one aspect, the memory 58 can store data or computer programs for use with the device 10. For example, the memory 58 may be used to store instructions for the vibrator 18. It is contemplated that the biofeedback may be proportional, in some respect, to the amount of teeth-clenching that is occurring (i.e., the force being applied to the bite portion, tab 14). Accordingly, as the force applied by the closing teeth increases, the stimulus (i.e., vibration by the vibrator 18) applied to the user likewise increases. Additionally, controls can be provided to allow the user to adjust how the system will respond. These could be amplitude adjustments as indicated in the preceding paragraph, whereby the impulse to the user varies with clenching force.

For example, the device 10 may have one or more settings relating to duration, amplitude, etc. of the vibration. The device 10 may use usage input to modify the input into a variety of outputs based on the settings. The setting could be based on clinical data, guess and check, patient demographics, etc. As an example, one bite for 1 second could trigger 2 seconds of vibratory output. In another example, the vibration may have a sinusoidal decay to ease the user back to sleep. These settings may be programmed by the user via the computing device(s) illustrated in FIG. 8, or even based on activating the vibrator in a certain sequence to enter a 'setup' mode. The device 10 can then emit a vibration to the user to communicate that it has or has not received the inputs when in 'setup' mode.

The memory 58 can also store data relating to a use of the device 10. For example, the memory 58 may record duration of teeth clenching, pressure/force of teeth clenching, time, intensity, etc., to create a log or history of the teeth clenching of the user. This data may then be uploaded or transmitted to one or more of the computing devices illustrated in FIG. 8. Without limitation, the memory 58 can include a non-transitory computer-readable recording medium, such as a hard drive, DVD, CD, flash drive, volatile or non-volatile memory, RAM, or any other type of data storage, for example.

Further details relating to an embodiment as adapted for the treatment of bruxism can be found in U.S. Pat. No. 9,827,137, the disclosure of which is hereby incorporated by reference in the present application.

Figure 6:
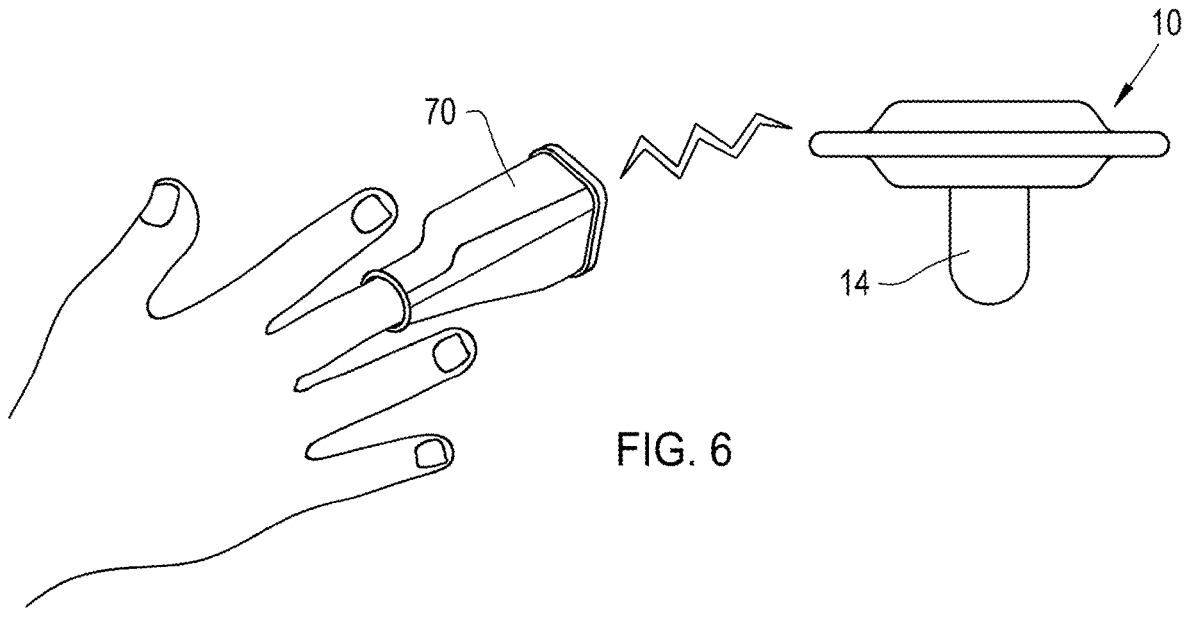
FIG. 6 is a schematic illustration of a device of the present disclosure as adapted for treatment of sleep apnea.

But as contemplated herein, the invention encompasses more than just the treatment of bruxism. Turning to FIG. 6, an embodiment using the device/chassis 10 is adapted for the treatment of sleep apnea. Here, one form of the invention uses a blood or pulse oximeter 70, which is intended to be applied to a user in standard fashion. It is known that in instances of prolonged breath stoppage, the blood oxygen level drops. If that level falls below a threshold, this can be an indication of an apnea episode. The oximeter thus functions as a trigger to reverse the apneic episode, that is, startle the sleeper, as through actuation of the vibrator 18 of the device 10, and reinstitute breathing.

In this form of the invention, the oximeter 70 would advantageously be connected to its own or an interconnected signal generator. The signal generated by the oximeter 70 is then transmitted to the device 10, for action. Device 10 therefore has a receiver 72 for the signal therein; this receiver is schematically illustrated as an optional feature of the block diagram FIG. 5.

There are other physiological phenomena that can be detected indicative of apnea, such as pulse rate, respiratory rate. These can also be used as thresholds for instituting action to break the episode. Also, the disclosure herein can be extended to deal with issues such as suffocation, and even Sudden Infant Death Syndrome.

The device 10 as a chassis may remain as generally described in its form for the treatment of bruxism. However, if used only for the treatment of some other issue, such as apnea or snoring, the tab 14 need not be adapted for the detection and response to teeth clenching. A modified tab 14' therefore is merely for positioning.

Figure 7:
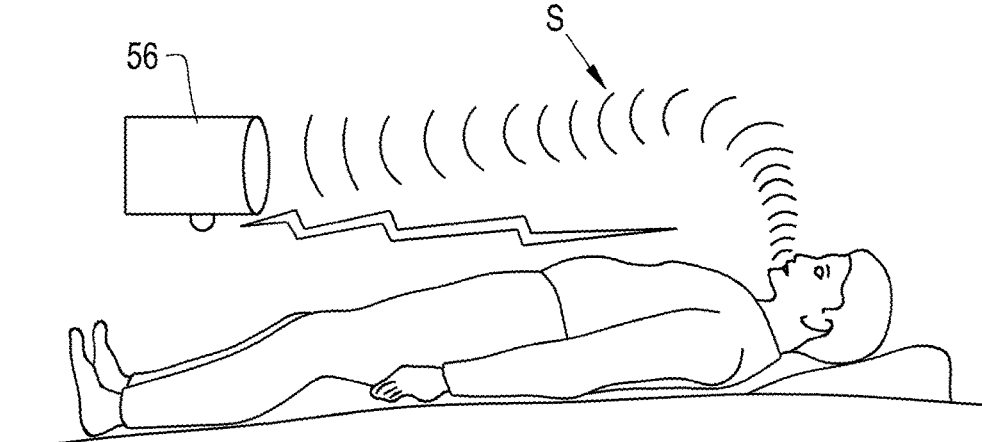
FIG. 7 is a schematic illustration of a device of the present disclosure as adapted for treatment of snoring.

Turning now to FIG. 7, what is schematically depicted is an adaptation for use in treating snoring. In this illustration, an Alexa-like apparatus 56 is located near or in the vicinity of the user, basically within a distance so as to hear the user. Apparatus 56 is programmed to detect the sounds S of an individual snoring, which may be a sonic or tonal level indicative of that person engaging in snoring. The apparatus 56 then sends a signal triggering the device 10 to provide a vibratory "nudge," and truncate the snoring episode.

As in the instance of apnea treatment, the tab 14 need not have contents adapted for teeth clenching, as its function here is also for location primarily.

Notably, and using the characteristic of this disclosure as a chassis 10, the device 10 can be adapted to contain all of the foregoing adaptations for bruxism, apnea and snoring, or just one or more of the foregoing. The chassis may be adapted to receive modules that contain the elements for treatment of a specific issue. This could take the form of a kit, where multiple different treatment modules can be swapped in and out, depending upon the need. The kit could therefore include the external peripheral apparati required.

Although systems, apparatuses, devices, and methods have been described and illustrated in connection with certain embodiments, many variations and modifications will be evident to those skilled in the art and may be made without departing from the spirit and scope of the disclosure. For example, the vibrator may be a piezoelectric device, a linear actuator, etc. Similarly, the trigger mechanism for causing the vibrator to activate may be a pressure sensitive switch or a contact switch. The disclosure is thus not to be limited to the precise details of methodology or construction set forth above as such variations and modification are intended to be included within the scope of the disclosure, and the Claims hereafter.

What is claimed is:

1. A system for treatment of bruxism, and one or more of snoring and sleep apnea or other sleep-related disorders, comprising:

a device as a chassis having an enclosure adapted to be held in a person's oral vestibule between an interior oral cheek wall and adjacent teeth, the enclosure having sidewalls and being sealed against fluid into an interior space of the enclosure;

an alert mechanism which provides a vibration through at least one sidewall of the chassis when actuated, or a visual stimulus, or an audible sound or alarm, or a vibration through a mechanism engaging or attached to a person but which is remote from the chassis;

a circuit which actuates the alert mechanism upon a signal; and a receiver within the enclosure included in the circuit configured to receive an externally generated signal from an apparatus external to the device, which externally generated signal is received by the receiver and actuates the alert mechanism;

wherein the apparatus external to the device has a mechanism that (1) determines whether a predetermined bruxism event, or a predetermined snoring event, or a predetermined sleep apnea event or other related sleep disorder has been detected, and (2) generates said signal, and a first module configured to treat bruxism, a second module configured to treat snoring and a third module configured to treat sleep apnea, each said module being adapted for separate operation and independent use in said chassis for treatment of a respective condition of bruxism, snoring and sleep apnea.

2. The system of claim 1, further including a pulse oximeter configured to be worn by a user during sleep, and a communication device configured to communicate with the oximeter, wherein the oximeter is configured to generate an oximeter signal when a blood oxygen level falls below a predetermined threshold and is therefore indicative of sleep apnea, and wherein the oximeter signal is configured to actuate alert mechanism.

3. The system of claim 1 further comprising:

an addition sensor, comprising one or more of a hydration sensor, a pulse oximeter, a respiration sensor, a Pleth index, a pedometer, a body position or actigraphy; and an IoT software interface adapted for use with a smart device or other receiver connected with an apparatus for registering communications from said additional sensor.

4. The system of claim 3, wherein said communications generate respective indications of hydration index, SPO2, pulse rate, pulse rate variability, respiration rate, Pleth variability index, perfusion index, pedometer, body position and actigraphy.

* * * * *